(12) United States Patent
Krause et al.

(10) Patent No.: US 9,770,421 B2
(45) Date of Patent: Sep. 26, 2017

(54) USES FOR IDEBENONE AND RELATED BENZOQUINONES IN METABOLIC DISORDERS AND OTHER PPAR α/γ RELATED DISEASES AND CONDITIONS

(71) Applicant: INDANIO BIOSCIENCE INC., Toronto (CA)

(72) Inventors: Henry Krause, Mississauga (CA); Jens Tiefenbach, Toronto (CA)

(73) Assignee: INDANIO BIOSCIENCE INC., Toronto (CA)

( * ) Notice: Subject to any disclaimer, the term of this patent is extended or adjusted under 35 U.S.C. 154(b) by 0 days.

(21) Appl. No.: 14/777,104

(22) PCT Filed: Mar. 14, 2014

(86) PCT No.: PCT/CA2014/000253
§ 371 (c)(1),
(2) Date: Sep. 15, 2015

(87) PCT Pub. No.: WO2014/138922
PCT Pub. Date: Sep. 18, 2014

(65) Prior Publication Data
US 2016/0022607 A1    Jan. 28, 2016

Related U.S. Application Data

(60) Provisional application No. 61/791,681, filed on Mar. 15, 2013.

(51) Int. Cl.
*A61K 31/122* (2006.01)

(52) U.S. Cl.
CPC ............................... *A61K 31/122* (2013.01)

(58) Field of Classification Search
CPC .................................................. A61K 31/122
See application file for complete search history.

(56) References Cited

U.S. PATENT DOCUMENTS

| 6,136,859 A * | 10/2000 | Henriksen | A61K 31/07 514/561 |
| 7,981,915 B2 * | 7/2011 | Freedman | A61K 31/198 514/396 |
| 2010/0215725 A1 * | 8/2010 | Schwarz | A61K 9/0019 424/450 |

OTHER PUBLICATIONS

Mantena et al., Free Radical Biology & Medicine, 2008;44:1259-1272.*

* cited by examiner

*Primary Examiner* — San-Ming Hui
(74) *Attorney, Agent, or Firm* — Norton Rose Fulbright Canada LLP; Jung-Kay Chin

(57) ABSTRACT

The present invention relates to the use of a 1,4-benzoquinone derived compound for the treatment of a disease or condition that is associated with peroxisome proliferator activated receptor (PPAR) activity in a mammal.

5 Claims, 14 Drawing Sheets

A

B(1)

B(2)

B(3)

Fig. 1
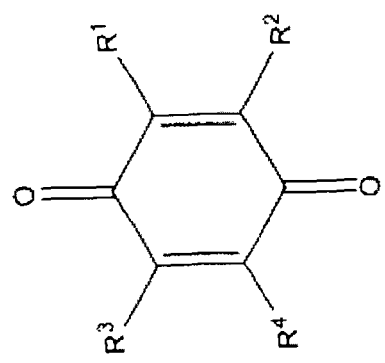
A
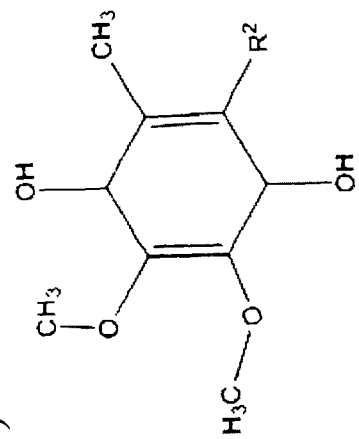
B(3)
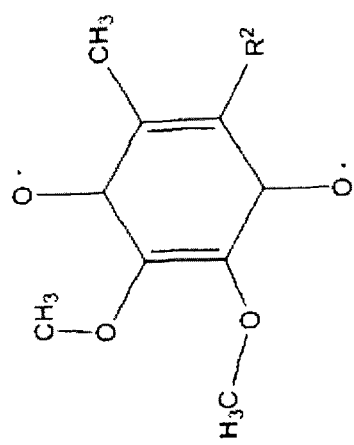
B(2)
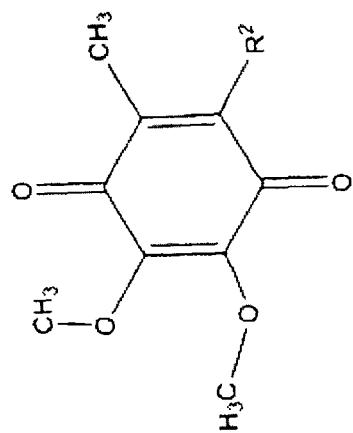
B(1)

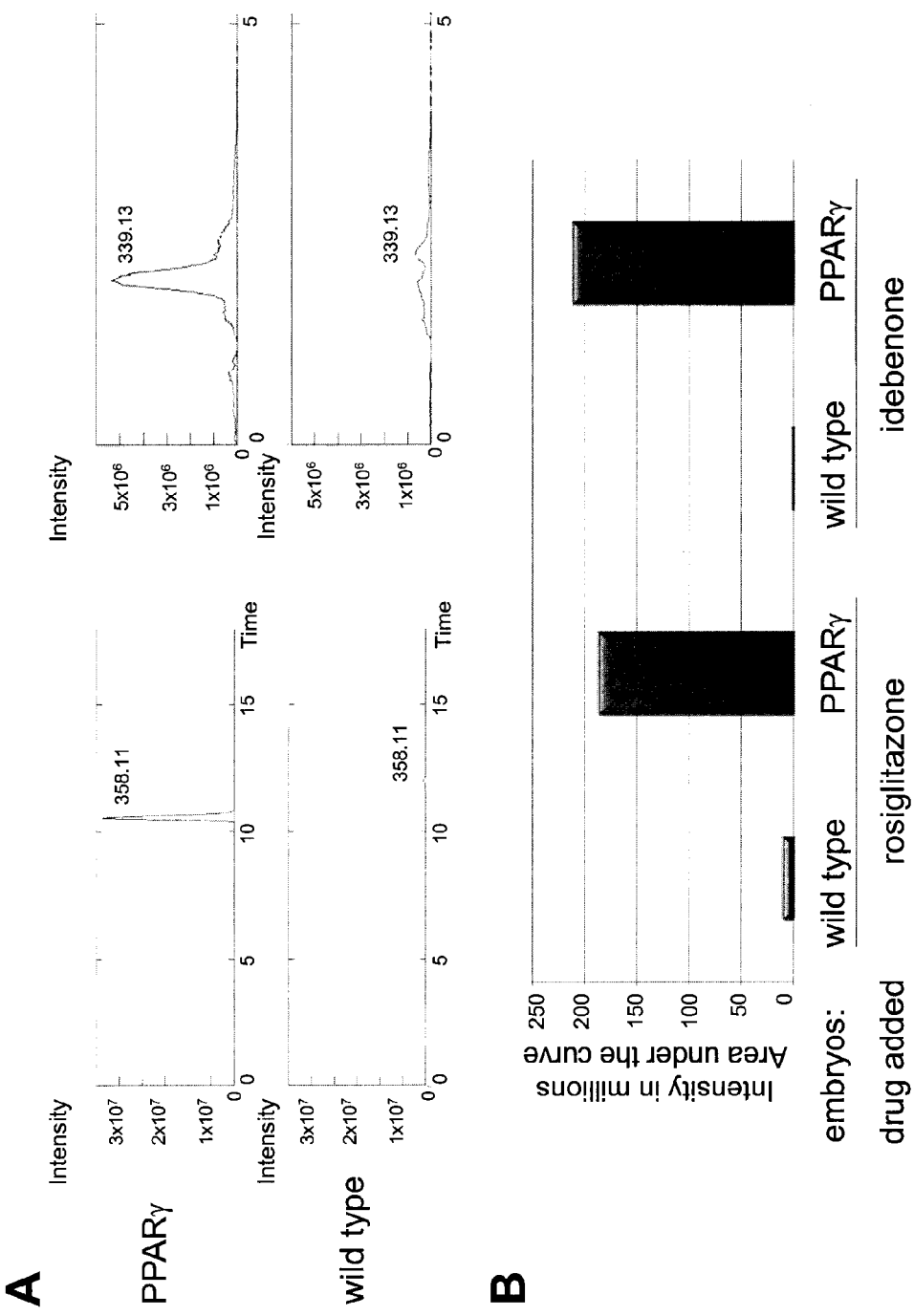

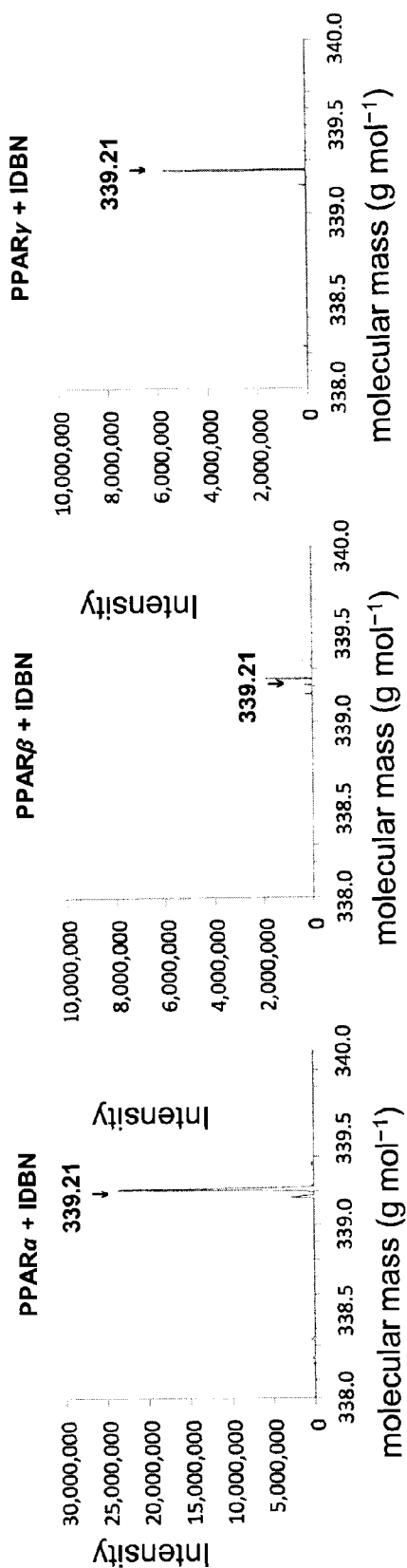

Fig. 9
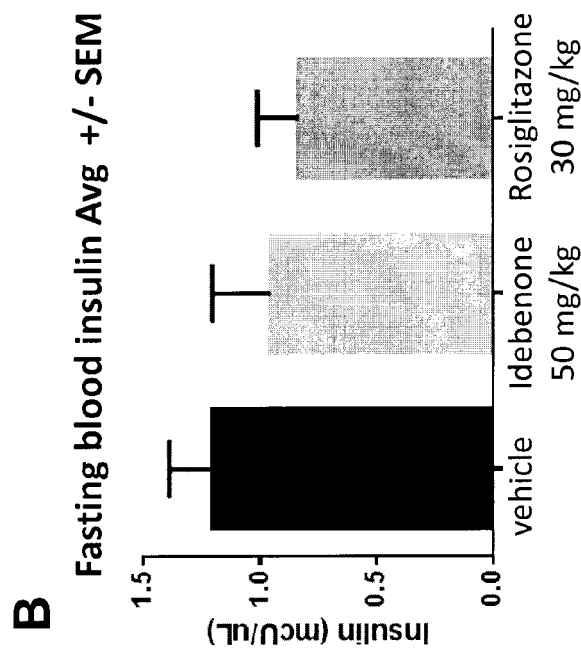
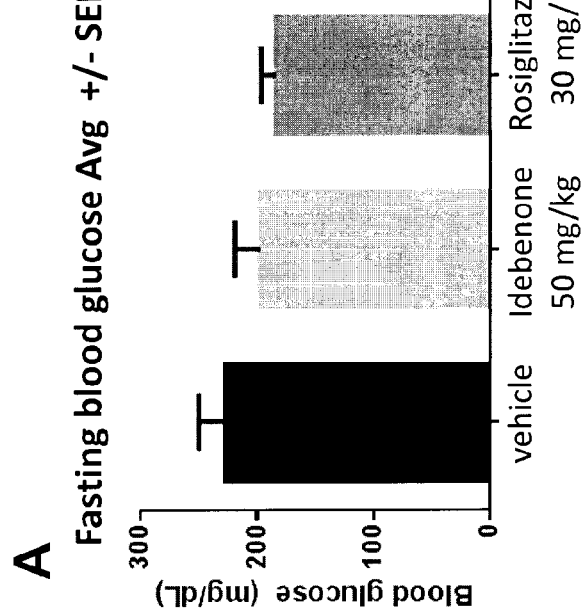
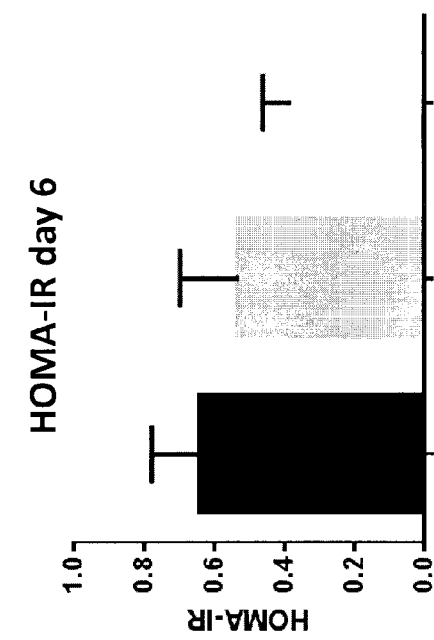

Fig. 11
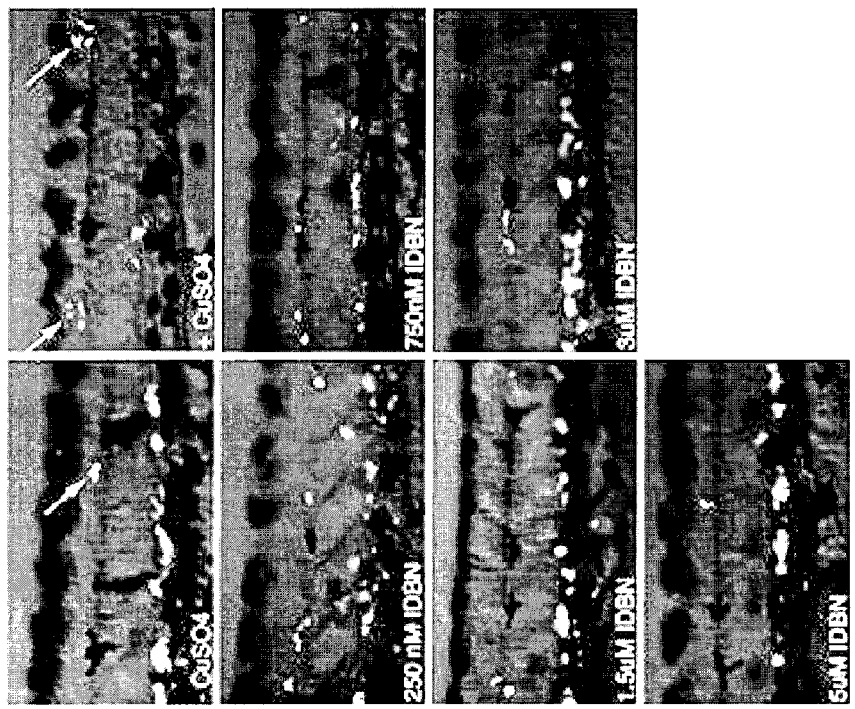
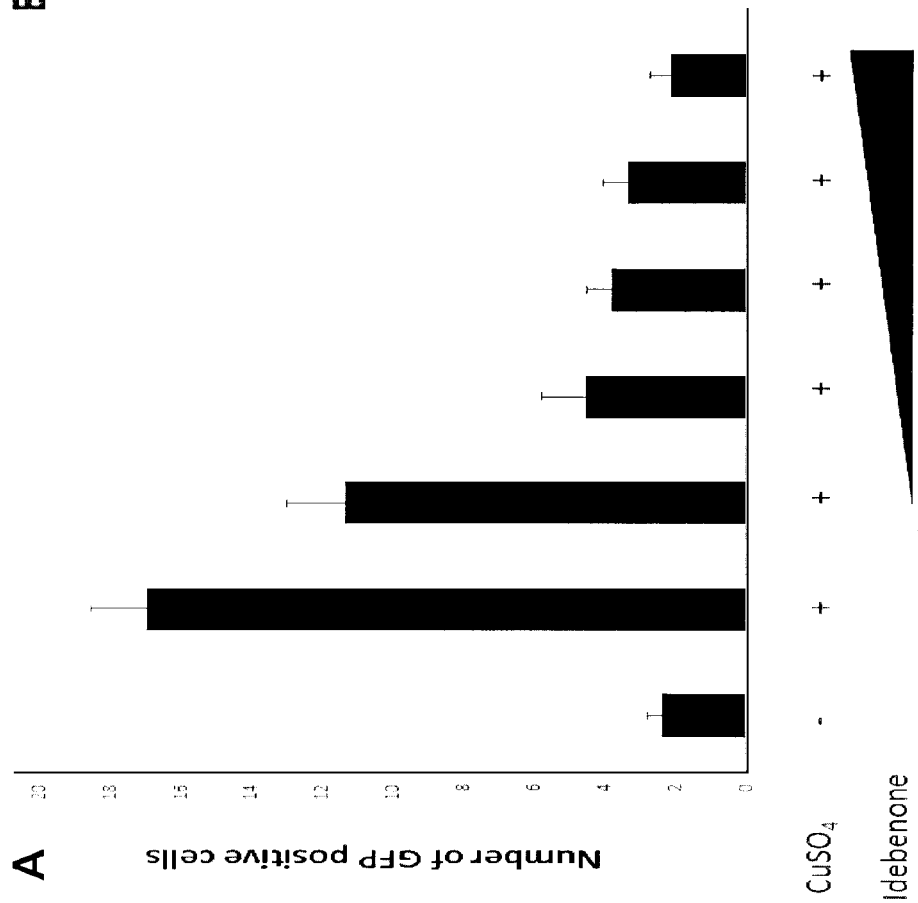

USES FOR IDEBENONE AND RELATED BENZOQUINONES IN METABOLIC DISORDERS AND OTHER PPAR α/γ RELATED DISEASES AND CONDITIONS

CROSS-REFERENCE TO RELATED APPLICATIONS

This application is a national phase application under 35 U.S.C. 371 of International Patent Application No. PCT/CA2014/000253 filed on Mar. 14, 2014, which claims priority from U.S. Provisional Patent Application No. 61/791,681 filed on Mar. 15, 2014.

FIELD OF THE INVENTION

The present invention relates to uses of compounds to treat PPAR related diseases and conditions. Specifically, certain embodiments of the present invention comprise the use of idebenone and related benzoquinones in treating PPAR α/γ related diseases and conditions.

BACKGROUND OF THE INVENTION

Nuclear receptors (NRs) are ligand-activated transcription factors that regulate the expression of target genes by recruiting co-activator or co-repressor complexes [1]. They are highly involved in diverse physiological processes such as metabolism, development, growth, reproduction and immunity [2-5].

Endogenous ligands or synthetic drugs that target NRs have been used to deal with many major and debilitating diseases. However, only a small percentage of NRs have been targeted, and even for these, drugs that act more selectively would provide huge benefits [6, 7]. New drugs capable of modulating orphan NR activities have the potential to control numerous additional disorders such as metabolic syndrome, cancer, inflammation, depression and anxiety.

Peroxisome proliferator-activated receptors (PPARs) are members of the NR superfamily. In humans, three PPAR genes have been characterized: PPARα, PPARδ (also known as PPARβ) and PPARγ. PPARα is highly expressed in metabolic tissues (brown adipose tissue, liver, kidney) but elevated levels are also present in the digestive (jejunum, ileum, colon, gall bladder) and cardiopulmonary (aorta, heart) systems. PPARα dysfunction is associated with susceptibility to hyperapobetalipoproteinemia, as well as a variety of cardiovascular (myocardial infarction, ischemic heart disease, atherosclerosis, hypertension), immune (psoriasis), metabolic (e.g.: plasma lipid levels, type II diabetes, body mass, plasma triglycerides and cholesterol, liver steatosis and steatohepatitis, hyperlipidemia, obesity, arterial blood pressure) and neurological (Alzheimer's disease) conditions.

PPARδ/β is ubiquitously expressed, and malfunction is most strongly associated with diseases such as colorectal cancer, atherosclerosis, hyperlipidemia, coronary heart disease, type II diabetes, obesity and Alzheimer's [8]. PPARγ is expressed at low levels in most physiology regulating tissues, including the central nervous system (CNS), gastrointestinal system, reproductive system, cardiopulmonary system and metabolic tissues, but is most highly expressed in brown and white adipose tissue. PPARγ dysfunction is associated with susceptibility to glioblastoma, familial partial lipodystrophy, atherosclerosis, hypertriglyceridemia, myocardial infarct, severe obesity, essential hypertension, type II diabetes, diabetic nephropathy, colon cancer, bladder cancer, breast cancer, lung cancer, non-Hodgkin's lymphoma, prostate cancer and skin cancer [9-13]. Associations with Alzheimer's disease, psoriasis and preterm delivery have also been observed [14].

PPARs belong to the "adopted orphan" subgroup of receptors. Although the identities of functionally relevant endogenous ligands have been determined, their physiological relevance is still somewhat controversial. The strongest case for PPARγ endogenous ligands include the lipoxygenase products 13-HODE and 15-HETE, the prostaglandins 15d-PGJ$_2$ (15-deoxy-Δ-prostaglandin J$_2$) and 15-ketoprostaglandin E$_2$-as well as lysophosphatidic acid (1-acyl-2-hydroxy-sn-glycero-3-phosphate, LPA) [15-19], and for PPARα the phospholipid 1-palmitoyl-2-oleoyl-sn-glycerol-3-phosphocholine (POPhtCho) and leukotriene B4 (LTB4) [20, 21].

In terms of PPAR-directed drugs and associated disease indications, PPARα agonists, such as fibrates, have proven to be highly effective in the treatment of lipid disorders, such as hyperlipidemia and dyslipidemia. For PPARγ, the best known drugs are the thiazolidinediones (TZDs), such as rosiglitazone (Avandia) and pioglitazone (Actos), which are used to treat Type II diabetes and other metabolic syndrome disorders. The latter have become the most deadly and costly diseases of today, and continue to escalate.

TZDs are also being used and tested for a number of other PPARγ related diseases, including Alzheimer's, cancer, preterm delivery [9-11, 22, 23], polycystic ovary syndrome (PCOS) [24], non-alcoholic steatohepatitis [25, 26], psoriasis [27] and autism [28]. However, despite their usefulness and potential, it has become increasingly clear that TZDs produce a number of serious side effects, some of which can prove lethal. These include weight gain, bone loss, hypertension, cardiac hypertrophy and cardiac arrest [29-31]. Recently though, it has been shown that PPARγ ligands that have partial or no agonist activity can still restore insulin sensitivity at similar levels as full agonists without the associated side effects [32].

PPARα is the main target of fibrate drugs, a class of amphipathic carboxylic acids (e.g. clofibrate, gemfibrozil, bezafibrate, and fenofibrate). Fibrates have a good safety profile in humans, increasing high-density lipoprotein (HDL) levels while decreasing triglyceride levels. However, nausea, stomach upset, and sometimes diarrhea have been reported and longtime usage over several years can cause gallstone formation.

Quinones are a class of compounds that can exist in the oxidized (I), semi-reduced (II) or reduced (III) states (FIG. 1B). The quinoid ring system, consisting of a fully conjugated cyclic dione structure [33] is the basic component of this large and important organic compound family. Quinones are involved in many cellular processes and are found in fungi, plants, animals and bacteria [33]. Quinones also share three additional properties; they are colored, strong antioxidants and electrophiles [33]. In humans, the prevalent form is CoQ$_{10}$, which is primarily found in peroxisomes and mitochondria. In peroxisomes, it is assumed to function primarily as a reducing agent of reactive oxygen species produced by metabolism. In the mitochondria, it is a component of complex II of the ATP-producing electron transport chain.

Idebenone is a synthetic analogue of CoQ$_{10}$ ([34]; compound of Formula I) initially developed by Takeda Chemical Industries, Ltd. (described in the specification for Japanese Patent Examined Publication No. 3134/1987) for the treatment of Alzheimer's disease and other cognitive diseases that might be associated with oxidative damage. Notably, it's relatively short ten-carbon alkyl tail with a terminal hydroxyl group makes it more soluble than $CoQ_{10}$. Like $CoQ_{10}$, however, it is a strong antioxidant, and has been shown to inhibit lipid peroxidation and to protect cell membranes and mitochondria from oxidative damage. Idebenone has also been shown to restore mitochondrial electron transport chain function and ATP formation when $CoQ_{10}$ or other complex II components are missing or inactive. Additional described activities include the inhibition of neuronal $Ca^{2+}$ channels [35] and anti-inflammatory properties that stem, at least in part, from the inhibition of prostaglandin synthesis [36].

Large clinical trials have shown that idebenone is safe and well tolerated in human subjects [37, 38]. The excellent safety profile of idebenone, and its mitochondrial and antioxidant activities, have more recently led to the investigation of its suitability for the treatment of diseases such as Friedrichs Ataxia, Mitochondrial Encephalomyopathy, Lactic Acidosis, Stroke-Like Syndrome (MELAS), Duchenne Muscular Dystrophy and most recently Leber's Hereditary Optic Neuropathy (LHON) [38-41].

SUMMARY OF THE INVENTION

In an aspect, there is provided use of a 1,4-benzoquinone derived compound for the treatment of a disease or condition that is associated with peroxisome proliferator activated receptor (PPAR) activity in a mammal.

In an aspect, there is provided a use of a 1,4-benzoquinone derived compound, in the manufacture of a medicament for the treatment or prevention of a disease or condition that is associated with a peroxisome proliferator activated receptor (PPAR) activity in a mammal.

In an aspect, there is provided a method of treating or preventing a disease or condition that is associated with a peroxisome proliferator activated receptor (PPAR) activity a mammal comprising: identifying a mammal in need of such treatment or prevention; and administering a therapeutically effective amount of a 1,4-benzoquinone derived compound.

In an aspect, there is provided a pharmaceutical composition for use in the treatment or prevention of a disease or condition that is associated with a peroxisome proliferator activated receptor (PPAR) activity in a mammal, comprising a therapeutically effective amount of a 1,4-benzoquinone derived compound and a pharmaceutically acceptable carrier.

In an aspect, there is provided a use of a 1,4-benzoquinone derived compound for modulating a peroxisome proliferator activated receptor (PPAR) activity in a mammal.

DESCRIPTION OF THE DRAWINGS

A detailed description of the preferred embodiments is provided herein below by way of example only and with reference to the following drawings.

FIG. 1 illustrates the structure of the compound of Formula (I) (A). In the case of Coenzyme Q (CoQ) molecules, the isoprenoid side chains can number from 0 (isoprenoid subunits) to 10. As demonstrated by a possible embodiment of Formula (I), compounds of Formula (I) can exist in the oxidized (B I), semi-reduced (B 2) or reduced (B 3) form (FIG. 1B).

FIG. 7 shows that rosiglitazone and idebenone co-purify with affinity-tagged PPARγ expressed in zebrafish. Wild type or LT-PPARγ embryos were incubated in 1 μM rosiglitazone spiked with 250 nM deuterated rosiglitazone, or 4 μM idebenone spiked with 250 nM $^{13}$C idebenone, followed by a 2-step affinity purification regimen carried out in 1M NaCl. Following purification, bound small molecules were extracted using 2:1 chloroform/methanol and subjected to LC-MRM (liquid chromatogaphy—multiple reaction monitoring) mass spectrometry to identify co-purifying small molecules. MRM profiles are shown in A) and relative abundance in B).

FIG. 9 shows that idebenone lowers blood glucose and fasting insulin levels in obese mice. Mice were fed on a high fat diet supplemented with vehicle, rosiglitzane or idebenone twice daily for 5 days. Blood glucose levels are shown in A), fasting insulin levels in B) and insulin resistance in C.

FIG. 11 demonstrates that idebenone has anti-inflammatory activity via PPAR activation. A) GFP-expressing leukocytes recruited in response to CuSO4 treatment were counted and graphed for the different treatment groups B) Representative zebrafish images of the different treatment groups are shown. Images show lateral views of the embryo and were taken using a fluorescent dissection scope (SteREO Lumar.V12 Carl Zeiss). GFP-expressing leukocytes are indicated by arrows.

DETAILED DESCRIPTION OF THE INVENTION

Figure 2:
FIG. 2 illustrates LT-PPARγ fish responding to pioglitazone and idebenone. In the ligand trap (LT) system, a GAL4 DNA-binding domain (DBD) human nuclear receptor ligand-binding domain (LBD) fusion protein is used to signal the presence of ligand in vivo. Binding of the fusion protein to a GAL4-dependent GFP reporter results in GFP expression when in the presence of specific ligands and cofactors. Here, LT-PPARγ transgenic embryos show strong reporter activation in the presence of the receptor-specific full agonist pioglitazone (B). Strong GFP expression is observed in the CNS, heart, blood, renal tube and eye. Idebenone treatment leads to more limited GFP expression in cells of the blood, epidermis and CNS (C). Overlay pictures of bright field and GFP (85% transparent) are shown. Views are lateral with anterior to the left.

Briefly, the present invention refers to known quinone-derived compounds of Formula (I) (FIG. 1A).

Here, we report new mechanisms of action for these Formula I compounds via their function as ligands and partial agonists of PPARα and PPARγ. These interactions explain many of the previously reported properties and uses of these compounds, as well as other potential PPARα and PPARγ related processes and diseases. We show that these compounds, including the more soluble benzoquinones, such as $CoQ_2$ and water soluble versions of $CoQ_{10}$, directly bind to the receptor ligand binding domains of both receptors, and activate them in a spatially restricted fashion. The actions observed here for compounds of Formula I in vitro and in vivo suggest that they will have multiple uses in metabolic syndrome-related diseases, without the majority of side effects observed with existing PPAR-directed drugs.

Our results indicate that benzoquinones modulate the activities of PPAR α and γ, which leads to subsequent effects on peroxisome and mitochondrial numbers, activities and interactions. These effects and the data presented herein, along with the strong safety record of Formula I compounds, suggest many new indications associated with PPARα/γ functions and diseases.

In an aspect, there is provided use of a 1,4-benzoquinone derived compound for the treatment of a disease or condition that is associated with peroxisome proliferator activated receptor (PPAR) activity in a mammal.

As used herein, "associated with peroxisome proliferator activated receptor (PPAR) activity" means any disease or condition wherein PPAR is directly or indirectly implicated in the disease or condition's pathogenesis. Examples of PPAR related diseases include, but are not limited to atherosclerosis, myocardial infarction, ischemic heart disease, chronic inflammation, psoriasis, Duchenne muscular dystrophy, kidney diseases including diabetic nephropathy, chronic cyclosporine nephropathy, glomerulonephritis, hypertensive nephrosclerosis, chronic cyclosporine nephropathy, glomerulonephritis, hypertensive nephrosclerosis and ischemiareperfusion injury, metabolic syndrome diseases including type 2 diabetes, obesity, hypertension and lipedemia, oxidative stress, free radical mediated injury, Alzheimer's disease, Huntington's disease, Parkinson's disease, steatosis, steatohepatitis, cancer including breast carcinoma, prostate carcinoma, lung carcinoma, esophageal squamous cell carcinoma (ESCC), colon carcinoma, ovarian carcinoma and skin carcinoma, amyotrophic lateral sclerosis, migraines, Leber's hereditary optic neuropathy, Friedreich's ataxia, bone hyperplasia, stroke, and gestational diseases including intrauterine growth restriction (IUGR), preterm birth, pre-eclampsia and gestational diabetes.

In an embodiment, the compound is of Formula (I), semi-reduced forms, reduced forms, salts, solvates, esters or prodrugs thereof,

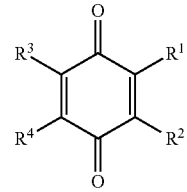

Formula (I)

wherein $R^1$, $R^2$, $R^3$ and $R^4$ are each independently H, or an organic group.

As used herein, "semi-reduced forms" means a compound of Formula (I) wherein one of the double bonded oxygen molecules to the main cyclic structure is reduced to a hydroxyl functional group.

As used herein, "reduced forms" means a compound of Formula (I) wherein both the double bonded oxygen molecules to the main cyclic structure is reduced to hydroxyl functional groups.

As used herein, "prodrugs" means a compound that, after administration, is metabolized or otherwise converted to an active or more active form with respect to at least one biological property, relative to itself.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

In some embodiments, $R^1$ represents a lower alkyl; $R^2$ represents a a hydrogen, an optionally substituted alkyl or an optionally substituted alkenyl; $R^3$ and $R^4$ each represents an optionally substituted lower alkyl or a lower alkoxy, or $R^3$ and $R^4$ form, taken together, a butadienylene. In certain preferred embodiments, R2 is one or more repeating isoprene units.

As used herein, "alkyl" means a group formed by removing a hydrogen from a carbon of an alkane, where an alkane is an acyclic or cyclic compound consisting entirely of hydrogen atoms and saturated carbon atoms. An alkyl group may include one or more substituent groups.

As used herein, "alkenyl" means a group formed by removing a hydrogen from a carbon of an alkene, where an alkene is an acyclic or cyclic compound consisting entirely of hydrogen atoms and carbon atoms, and including at least one carbon-carbon double bond.

As used herein, "lower alkyl" means a group formed by removing a hydrogen from a carbon of an alkane having one to 10 carbon atoms, where an alkane is an acyclic or cyclic compound consisting entirely of hydrogen atoms and having one to 10 saturated carbon atoms. As used herein, "optionally substituted" means that the group in question may either carry a substituent or may be unsubstituted.

As used herein, "lower alkoxy" means an alkyl group having one to 10 carbon atoms, wherein at least one carbon is singularly bonded to oxygen, i.e. R—O.

In an embodiment, $R^1$ is a $C_{1-4}$ alkyl; $R^2$ is (a) hydrogen, (b) a $C_{1-22}$ alkyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen, or (c) a $C_{2-15}$ alkenyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen; $R^3$ and $R^4$ each is a $C_{1-6}$ alkyl which may be substituted by 1 to 3 substituents selected from the group consisting of hydroxy, halogen, nitro, $C_{1-3}$ alkyl which may be halogenated, carboxy, $C_{1-6}$ alkoxy-carbonyl, 3-pyridyl, 1-imidazolyl and 5-thiazolyl or a $C_{1-3}$ alkoxy; or $R^3$ and $R^4$ form, taken together with the respective adjacent carbon atoms, a benzene ring which may be substituted by 1 to 3 substituents selected from the group consisting of $C_{1-3}$ alkyl, $C_{1-3}$ alkoxy, hydroxy, nitro and halogen.

In an embodiment, the compound is selected from the group consisting of idebenone (IDE, 2-(10-hydroxydecyl)-5,6-dimethoxy-3-methyl-2,5-cyclohexadiene-1,4-dione), coenzyme $Q_{10}$ ($CoQ_{10}$), coenzyme $Q_9$ ($CoQ_9$), coenzyme $Q_8$ ($CoQ_8$), coenzyme $Q_7$ ($CoQ_7$), coenzyme $Q_6$ ($CoQ_6$), coenzyme $Q_5$ ($CoQ_5$), coenzyme $Q_4$ ($CoQ_4$), coenzyme $Q_3$ ($CoQ_3$), coenzyme $Q_2$ ($CoQ_2$), coenzyme $Q_1$ ($CoQ_1$) and Coenzyme $Q_0$ ($CoQ_0$).

In some embodiments, the compound is idebenone.

In some embodiments, the compound is selected from the group comprising; $CoQ_{10}$, $CoQ_9$, $CoQ_8$, $CoQ_7$, $CoQ_6$, $CoQ_5$, $CoQ_4$, $CoQ_3$, $CoQ_2$, $CoQ_1$ and $CoQ_0$, preferably $CoQ_{10}$.

In some embodiments, the disease or condition is associated with a PPAR deficiency or would be ameliorated by PPAR activation.

As used herein, "associated with a PPAR deficiency" means any disease or condition associated with peroxisome proliferator activated receptor (PPAR) activity wherein disease or condition pathogenesis is associated with reduced or lessened expression, function or presence of PPAR receptors.

As used herein, "ameliorated by PPAR activation" means any disease or condition associated with peroxisome proliferator activated receptor (PPAR) activity wherein the disease, condition, or signs and/or symptoms thereof in a subject are reduced, lessened or bettered by an agonistic effect on PPAR.

In some embodiments, the PPAR is PPAR alpha.

In some embodiments, the PPAR is PPAR beta.

In some embodiments, the PPAR is PPAR gamma.

In some embodiments, the disease or condition is a metabolic syndrome disease.

As used herein, "metabolic syndrome disease" refers to or describes the physiological condition in mammals that is typically characterized by obesity, insulin resistance, hyperlipidemia, and hypertension. It may further encompass vascular abnormalities such as endothelial dysfunction, vascular pro-inflammatory condition, and vascular pro-coagulative conditions. Metabolic syndromes also refer to syndromes accompanied by health risk factors such as hypertriglyceridemia, hypertension, glycometabolism disorders, blood coagulation disorders and obesity.

In some embodiments, the disease or condition is type 2 diabetes mellitus.

In some embodiments, the disease or condition is hypertension.

In some embodiments, the disease or condition is obesity.

In some embodiments, the disease or condition is selected from the group comprising; non-alcoholic fatty liver disease steatosis and steatohepatitis.

In some embodiments, the disease or condition is selected from the group comprising; hyperlipidemia and hypertriglyceridemia.

In some embodiments, the disease or condition is psoriasis.

In some embodiments, the disease or condition is a kidney disease. Preferably, the kidney disease is selected from the group comprising; diabetic nephropathy, chronic cyclosporine nephropathy, glomerulonephritis, hypersensitive nephrosclerosis and ischemia-reperfusion injury.

In some embodiments, the disease or condition is a gestational disease.

Preferably, the gestational disease is selected from the group comprising; intrauterine growth restriction (IUGR), preterm birth, pre-eclampsia and gestational diabetes.

In some embodiments, the disease or condition is bone hyperplasia.

In some embodiments, the disease or condition is a cancer. Preferably, the cancer is selected from a group comprising breast carcinoma, prostate carcinoma, lung carcinoma, esophageal squamous cell carcinoma (ESCC), colon carcinoma, ovarian carcinoma, and skin carcinoma.

In some embodiments, the disease or condition is steatohepatitis.

In an aspect, there is provided a use of a 1,4-benzoquinone derived compound, in the manufacture of a medicament for the treatment or prevention of a disease or condition that is associated with a peroxisome proliferator activated receptor (PPAR) activity in a mammal.

In an aspect, there is provided a method of treating or preventing a disease or condition that is associated with a peroxisome proliferator activated receptor (PPAR) activity a mammal comprising: identifying a mammal in need of such treatment or prevention; and administering a therapeutically effective amount of a 1,4-benzoquinone derived compound.

In an aspect, there is provided a pharmaceutical composition for use in the treatment or prevention of a disease or condition that is associated with a peroxisome proliferator activated receptor (PPAR) activity in a mammal, comprising a therapeutically effective amount of a 1,4-benzoquinone derived compound and a pharmaceutically acceptable carrier.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In an aspect, there is provided a use of a 1,4-benzoquinone derived compound for modulating a peroxisome proliferator activated receptor (PPAR) activity in a mammal.

The present invention will be understood by reference to the following non-limiting examples.

EXAMPLES

Materials & Methods
Transgenic Fish Line Generation and Maintenance

Zebrafish were maintained at 28.5° C. on a 14/10 hour light/dark cycle and staged according to hours (h) or days (d) postfertilization [43]. To generate pLT PPARα (aa 178-468) and pLT PPAR γ (aa 188-477) lines, plasmids were pre-digested with I-SceI (0.8 µg DNA, 1 µl I-SceI (New England Biolabs) 2 µl 10×I-SceI buffer, 1 µl BSA) for 20 min at 37° C. Digested DNA was adjusted with 0.1% phenol red. 4.6 nl of DNA solution was injected into the blastomeres of early one-cell stage embryos [44].

F0 fish were crossed with WT fish to identify germ-line transformed animals, as determined by agonist treatments and GFP expression. F1 progeny showing strong and consistent GFP responses were selected for F2 homozygote production. To avoid reporter GFP silencing of stable transgenic LT lines, homozygous fish showing strong and consistent GFP responses were selected for continued propagation of next generations.

Compound Screening

PPARγ ligand trap zebrafish screens were performed under optimized conditions in 96-well format using the ImageXpress Velos Laser Scanning Cytometer. 1 or 2 dpf embryos were heat induced (28→37° C.) for 30 minutes, de-chorionated and then arrayed in 96-well plates (5 per well). Embryo water (0.075 g/L NaHCO3, 0.018 g/L Sea salt, 0.0084 g/L $CaSO_4 2H_2O$) was removed and 200 µl of fresh embryo water/well including dissolved small molecules or solvent was added. The Enzo FDA approved drug library (BML-2841-0100/640 compounds) was used for drug repositioning and screened at three different concentrations (1, 3 or 10 µM final concentration). Embryos were incubated at 28° C. for 14 h, anesthetized with Tricaine (Sigma, Cat. # A-5040) and then analyzed for GFP fluorescence using the ImageXpress Velos Laser Scanning Cytometer.

Murine 3T3-L1 Adipocyte Differentiation Assay

The cell line was originally obtained from ATCC and 3T3-L1 cells were maintained in the fibroblasts stage in DMEM (Gibco: 11995-065), 10% FBS (Gibco: 26140-079) and Pen-Strep solution (Gibco: 15140-122). Cells were grown in 75 $cm^2$ flasks and sub-cultured just prior to confluence. Medium was removed and washed twice with PBS. For cell differentiation 2 day post-confluent monolayers were incubated for 2 days in DMEM containing: 10% fetal bovine serum (FBS), 100 µg/ml IBMX (from a 500× stock in 0.15 M KOH, prepared fresh), 390 ng/ml dexamethasone (from a 1000× stock in EtOH) and 5 µg/ml insulin (from a 1000× stock in 0.1 M HCl). After 2 days media was replaced with DMEM+ 10% FBS and 5 µg insulin only and cells were maintained for another 2 days. Media was then replaced by DMEM+ 10% FBS for 5-6 days until differentiation was complete. After differentiation media was removed and cells were washed twice with PBS and then fixed in 4% PFA. Lipids were stained with Oil O red.

Cell Culture Reporter Assay

Human HEK293 embryonic kidney cells were maintained in DMEM, 10% FBS and Pen/Strep. Transfection was carried out using calcium phosphate with indicated expression constructs and respective luciferase reporters. Treatment of the cells with ligands was carried out one day after transfection. After 48 hours cells were lysed. Luciferase values were normalized for transfection efficiency using β-galactosidase and expressed as Relative Luciferase Units (RLU) from triplicate assays. Plasmids. pCMX, pcDNA3-GAL4-hPPARα (aa 178-468), pcDNA3-GAL4-hPPARδ/β (aa 143-441), pcDNA3-GAL4-hPPARγ (aa 188-477), UAS-luc, pGEM, pCMX-β-galactosidase.

Chemicals

Alexis Biochemicals: Pioglitazone (ALX-270-367); Cayman Chemicals: Rosiglitazone (#71740); GW7647 (#10008613) and CAY10592 (#10012536); BIOSYNTH International, Inc.: Idebenone (Q-201229); Toronto Research Chemicals Inc. (TRC) Rosiglitazone-d3, 1 mg (cat# R693502), Santa Cruz: Idebenone-13Cl,d3 (sc- 280816); Sigma-Aldrich: Idebenone (#I5659), CoQ0 (#D9150), CoQ1 (#C7956), CoQ2 (#C8081) 1,4-Benzoquinone (#51386) Dimethyl sulfoxide (#D8418); Bioshop: Acetone (#ACE888.500); Inno-Vite Inc.: CoQ10 Li-Q-Sorb (NPN80007078), MitoQ was a gift from Mike Murphy [MRC Mitochondrial Biology Unit/Wellcome Trust/MRC Building/Hills Road/Cambridge/CB2 0XY/United Kingdom]

Protein Purification

Protein expressed in *E. coli* was purified using Ni-NTA affinity chromatography as described elsewhere [45].

Stargazer Analyses

Rosiglitazone, idebenone and $CoQ_0$ were screened for direct binding to human PPARγ LBD (residues 206-477), expressed in pRSET and purified from BL21 codon plus bacteria, using the Stargazer assay (Affinium Parmaceuticals). Briefly, protein samples were heated from 27° C. to 80° C. at the rate of 1° C. per minute in clear bottom 384 well plates (Nunc), and protein aggregation was monitored. Images of scattered light were captured every 30 s and the light intensities were translated to arbitrary numbers. Intensities were plotted against temperature for each sample well. The midpoint of each transition was identified and is referred to as the transition temperature. Each well contained 50 μl of 0.2 mg/ml PPARγ LBD, 200 mM Tris (pH 7.5), 150 mM NaCl and indicated ligands covered by 50 μl of mineral oil. Each ligand was tested in duplicate.

Affinity Purification of PPAR Ligands 1 dpf zebrafish embryos were heat induced for 1 hr in pre-heated embryo water 37° C. (+/– drugs). Following a 1 hr 30 min recovery at 28.5° C., embryos were frozen in liquid nitrogen. Purification steps were performed at 4° C. Frozen embryos were homogenized in lysis buffer (50 mM Hepes ph7.5, 1M NaCl, 0.1% Triton X-100, 1 mM DTT, 1 mM EDTA, 1 ppm BHT, Complete protease inhibitor cocktail tablet (Roche, 1 tablet/50 ml buffer)) at a ratio of 4 ml lysis buffer/gram embryos. After 20 min incubation on ice, the lysate was centrifuged at 14000×g for 15 mins. The supernatant was passed through a column of pre-washed (lysis buffer) avidin-conjugated agarose slurry (Pierce, #20219; 1:30 slurry:lysate) and the resulting flow-through incubated with anti-FLAG M2 affinity gel (Sigma-Aldrich, #A2220; 1:150 slurry:lysate) for 2 hrs. After incubation the beads were transferred to a 2 ml-gravity disposable column (Biorad, #732-6008), washed 3 times with 6 column volumes (bead volume) of lysis buffer and eluted three times with 4, 3 and 3 column volumes of 300 ug/ml 3×FLAG peptide dissolved in lysis buffer (each elution requires 30 mins incubation). The Flag elutions were combined and incubated with StrepTactin slurry (IBA, #2-1201-0251; 1:5 slurry:flag elution) for 1.5 hrs. The beads were then transferred to a 2 ml-gravity disposable column and washed 3 times with 6 column of Last Wash Buffer (800 mM ammonium acetate pH7.5, 1 ppm BHT). The beads were then transferred to a glass vial and the samples prepared for mass spectrometry.

Mass Spectrometry Analysis of Drugs Bound to the NRs

The beads from affinity purification were treated with 2:1 chloroform/methanol (in a ratio of 1:4, beads/solution:chloroform/methanol) and then centrifuged. The chloroform phase was collected and dried under a stream of nitrogen gas. The dried residue was reconstituted in 10% acetonitrile prior to LC-MRM. LC-MS analysis was performed on a triple quadrupole mass spectrometer (Quattro Micro™, Micromass, Manchester, UK) coupled with an Agilent 1100 HPLC. A reverse phase column (Luna C-18(2); 3 mM, 1.00 mm×15 cm, Phenomenex, Torrance, Calif.) was used for LC separation, with an elution gradient starting at 0.005% formic acid, 5% acetonitrile in water (buffer A) at time zero, with a flow rate of 70 ml/min, increasing to 0.05% formic acid, 50% acetonitrile in water (buffer B) by 10 min, kept stable for 5 min, and then increasing to 0.095% formic acid, 95% acetonitrile in water (buffer C) over the next 5 min and then returning to Buffer A over the next 5 min. General MS conditions were as follows: Capillary voltage was 3.5 kV, cone voltage was 30 V, and LM/HM resolution for both MS and MS2 was set to 15/15 so that a resolution of 1100 at FWHM was achieved for peak at 370 m/z. For LC-MRM, argon was used as a collision gas at a pressure of $3.1 \times 10^{-3}$ mbar. MRM conditions for each drug were as follows: Rosiglitazone (ES+, transition 358 - - - 135. Collision Cell Voltage 27V), Idebenone (ES+, transition 339 - - - 197. Collision Cell Voltage 18 V).

Mouse Studies

Mouse-based biomedical research was performed by the Jackson Laboratory to test the efficacy of idebenone in a diet-induced-obese (DIO) mouse model and approved by the Institutional Animal Care and Use Committee (IACUC). To test the efficacy of idebenone in a db/db mouse model experiments were performed at the Univerity of Torotno and were approved by the Animal Care Committee at the University of Toronto.

DIO study: Forty four (44) diet-induced obese C57BL/6J male mice (started on high fat diet at the age of 6 weeks) were used at 16 wks of age. The mice were ear notched for identification using the standard mouse ID format. Mice were housed at a density of 3-4 per cage in polycarbonate cages, which were both individually and positively ventilated. Bed-o'Cobs® corn cob bedding was provided and was changed every two weeks or as needed.

The animal room was lighted entirely with artificial fluorescent lighting on controlled 12 hr light/dark cycle (6 a.m. to 6 p.m. light). The normal temperature and relative humidity ranges in the animal rooms were maintained at 22±4° C. and 50±15%, respectively. The animal room was set for 15 air exchanges per hour. Filtered tap water acidified to a pH of 2.5 to 3.1 was provided ad libitum. High fat diet (60 kcal %) was provided ad libitum. Following a 2 week acclimation, 32 mice were chosen based on desired body weight range. Remaining mice were euthanized. Mice were randomized by body weight into four treatment groups (n=8) by body weight and non-fasting blood glucose taken three days prior to the start of dosing. Body weights, non-fasting blood glucose, and insulin were measured before dosing. Dosing occurred for 5 days. Fasting blood glucose and insulin were measured at the end of dosing (mice were fasted overnight on day 5, and insulin and blood glucose was measured on day 6). Mice were euthanized by $CO_2$ euthanasia. An aliquot of whole blood was processed to measure insulin.

Treatment Protocol to Test the Efficacy of Idebenone in a Diet-Induced-Obese (DIO) Mouse Model

| Gp | n | Treatment | Dose (mg/kg) | Dose Route | Dose Regimen |
|---|---|---|---|---|---|
| 1 | 8 | Vehicle | n/a | PO | 2x daily, for 5 days |
| 2 | 8 | Idebenone | 50 | PO | 2x daily, for 5 days |
| 3 | 8 | Idebenone | 200 | PO | 2x daily, for 5 days |
| 4 | 8 | Rosiglitazone | 30 | PO | 2x daily, for 5 days |

Db/db study: Forty male C57Bl/6 db/db mice (called B6.BKS(D)-Lepr db/J) were ordered from Jackson Laboratories (#000697) at 7 weeks of age. Mice were housed individually with free access to food (2016 Teklad Global 16% Protein Rodent Diet) and water on a 14 hour light/dark cycle (6 a.m. to 8 p.m. light). 10% sucrose and 100 µL Tween-80 was added to 300 g food which was supplemented with either vehicle (DMSO), 10 mpk rosiglitazone, 900 mpk idebenone or 1800 mpk idebenone. Food was exchanged on a daily bases. Harlan corn cob bedding was provided and was changed every week or as needed. Following a 1 week acclimation, 32 mice were chosen based on desired body weight range. Remaining mice were euthanized. Mice were randomized by body weight into four treatment groups (n=8) by body weight. Dosing occurred for 21 days. Mice were euthanized by $CO_2$ euthanasia and livers were fixed in neutral buffered formalin (NBF) for 24 h, followed by a one day fixation in 30% Sucrose and 10% Sucrose. Oil O Red staining was performed through the Pathology Research Program at the University Health Network in Toronto [46]. Treatment Protocol to Test Efficacy of Idebenone in a Diabetic db/db Mouse Model

| Gp | n | Treatment | Dose (mg/kg) | Dose Route | Dose Regimen |
|---|---|---|---|---|---|
| 1 | 8 | Vehicle | n/a | Food | daily, for 21 days |
| 2 | 8 | Idebenone | 900 | Food | daily, for 21 days |
| 3 | 8 | Idebenone | 1800 | Food | daily, for 21 days |
| 4 | 8 | Rosiglitazone | 10 | Food | daily, for 21 days |

TBARS Assay 100 mg of db/db livers were homogenized in RIPA buffer and protein concentration was quantified using a BCA protein assay kit (Cell signalling #7780) followed by measurement of 'Thiobarbituric Acid Reactive Substances' (TBARS) using a TBARS assay kit (Cayman Chemicals #10009055).

RNA Isolation, cDNA Synthesis and Real-time QPCR Analysis.

Total RNA was extracted from 100 mg of db/db livers using RNA STAT-60 (Tel-Test, Inc.), treated with DNase I (RNase-free, Roche), and reverse transcribed into cDNA with random hexamers using the High Capacity Reverse transcription system (Applied Biosystems, ABI). Primers used are shown below and were validated as previously described. Real-time QPCR reactions were performed on an ABI 7900 in 384-well plates containing 12.5 ng cDNA, 150 nM of each primer, and 5 µl 2×SYBR Green PCR Master Mix (ABI) in a 10 µl total volume. Relative mRNA levels were calculated using the comparative Ct method normalized to cyclophilin mRNA.

Primer for QPCR:

| PLIN4 F primer | CTTCCAGATGACAGACATGACCAT |
|---|---|
| PLIN4 R primer | ATGGTGTTCAAGCTCTGGTCACT |
| ADFP/PLIN2 F primer | GGAGGAAAGACTGCCTATTCTGAA |
| ADFP/PLIN2 R primer | CCATGGTAGTCGTCACCACATC |

Zebrafish Inflammation Assay:

Assay was performed as described in [47]. Fifteen dechorionated 55 hpf (hours post fertilization) embryos were transferred in each well of 6-well plates in 6 ml of embryo water. Idebenone was added at increasing concentrations (0.25, 0.75, 1.5, 3 and 5 µM). Embryos were incubated in the dark for 1 hr at 28 C, followed by a second 40 min incubation with copper sulfate ($CuSO_4$) at a final concentration of 10 µM at 28 C in the dark. Embryos were then transferred to Eppendorf tubes and fixed in 4% paraformaldehyde in 1×PBS overnight at 4 C in the dark. Numbers of GFP+ cells were counted along the lateral line/neuromast clusters.

A Zebrafish Based Screen of FDA-approved Drugs Yields a Novel PPARγ Agonist

Figure 3:
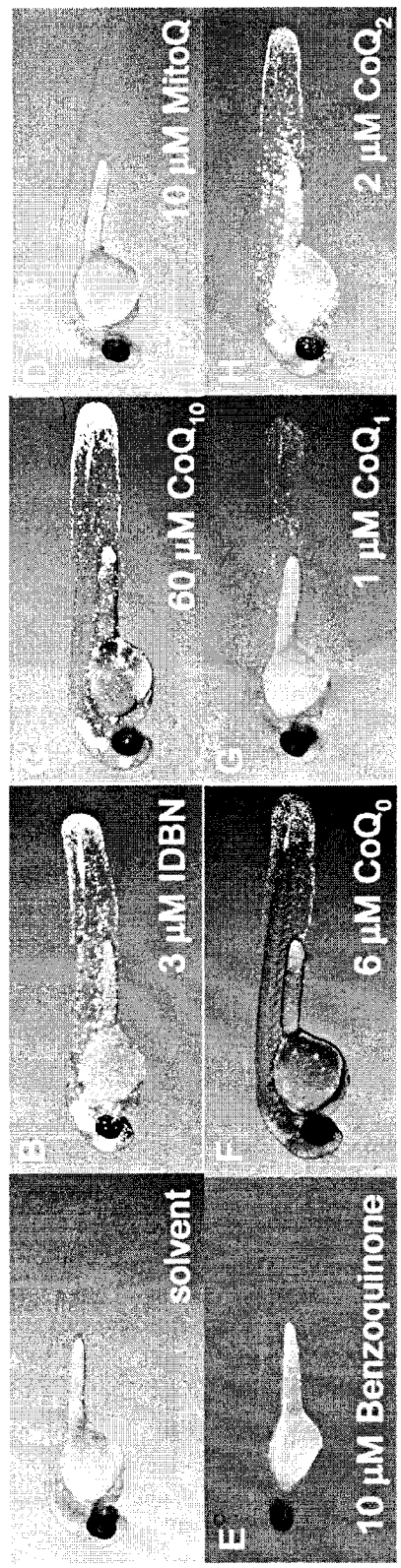
FIG. 3 illustrates that $CoQ_{10}$ and other CoQs also activate PPARγ. PPARγ LT embryos show very limited GFP expression in a small subset of epidermal cells and in the posterior spinal cord in the absence of exogenous ligand (A). Treatment with Idebenone (B) and $CoQ_{10}$ (C) induce similar patterns of GFP expression in cells of the epidermis, blood, CNS, and posterior spinal cord. A variant of idebenone that is targeted to the mitochondria (MitoQ) showed no activation (D). Likewise, benzoquinone, which contains only the 1 and 4 keto groups on the benzene ring, showed no reporter activation (E). $CoQ_0$ (F) and $CoQ_1$ (G), however, elicited weak PPARγ activation, while $CoQ_2$ (H) elicited similar levels of activation as $CoQ_{10}$ and idebenone. Overlay pictures of bright field and GFP (85% transparent) of 48 hpf embryos are shown. Views are lateral with anterior to the left.
Figure 4:
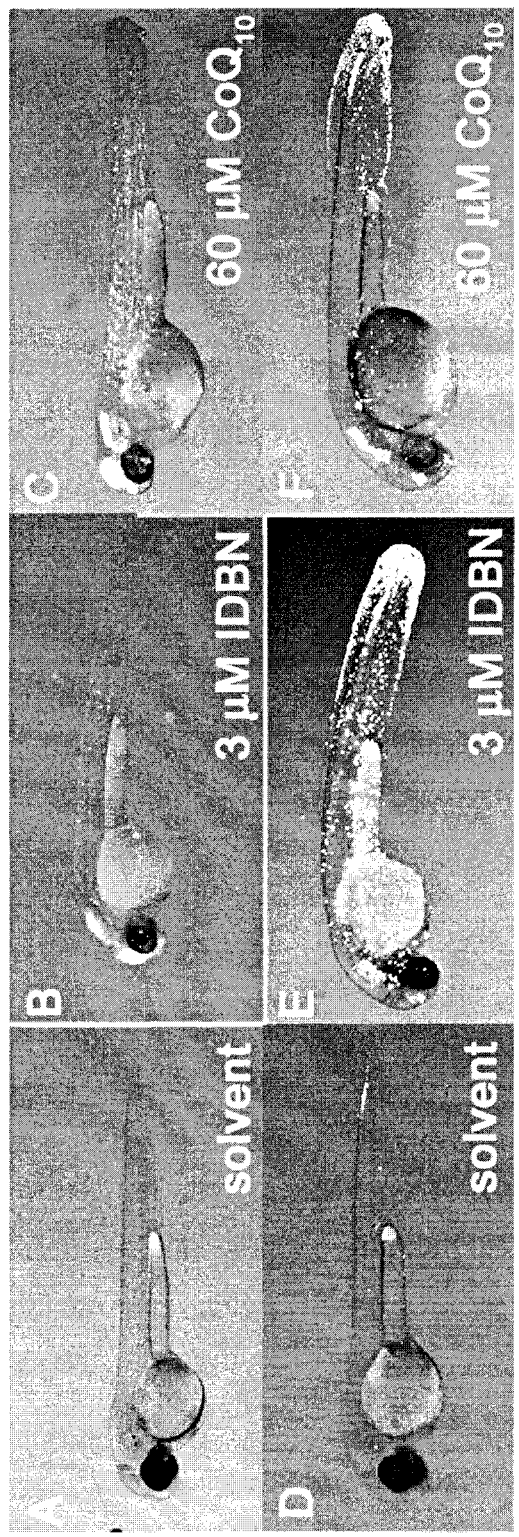
FIG. 4 shows that idebenone and $CoQ_{10}$ are dual agonists for PPARα and PPARγ. Transgenic PPARα(A-C) and PPARγ (D-F) LT embryos show unique GFP patterns in the absence of exogenous ligand (A, D) and in the presence of $CoQ_{10}$ (B, E) or idebenone (C, F). Overlay pictures of bright field and GFP (85% transparent) of 48 hpf embryos are shown. Views are lateral with anterior to the left.

In previous work, we developed a set of transgenic "ligand trap" zebrafish lines for human NR ligand identification and screening (PCT/CA2006/002114; [33]. In this system, the presence of agonists results in expression of a GFP reporter. This is easily detected using a fluorescence microscope or an automated laser cytometer system (eg: ImageXpress Velos Laser Scanning Cytometer). Here, we used a transgenic line representing the human nuclear receptor PPARγ to screen a 640 compound library of FDA-approved drugs (Enzo; BML-2841-0500). At screening concentrations of 1, 3 and 10 µM, a total of 42 hits were obtained, including 25 previously demonstrated PPARγ ligands such as the well-known TZD drugs troglitazone and pioglitazone (Table 1). The 17 novel hits included a number of interesting compounds, such as calcium channel blockers, immunosuppressants and a phosphodiesterase inhibitor (Table 1). Also included was the $CoQ_{10}$ analog idebenone. Idebenone yielded maximal activation in our fish reporter system when provided at a concentration of 4 µM or higher (FIG. 2). Notably, at this maximum response, GFP expression was weaker and less widespread than responses to rosiglitazone or pioglitazone, suggesting that idebenone is a partial agonist with a more restricted subset of responsive tissues (epidermis, blood and partial CNS for idebenone versus epidermis, blood, CNS, eye, and heart for the TZDs; FIGS. 3, 4).

Drug Hits Activating the PPARγ Ligand Trap Reporter Fish Line from the ENZO FDA Approved Library

TABLE 1

42 hits were obtained screening the human PPARγ ligand trap fish line.

| # SM hit | Target/classification | # SM hit | Target/classification |
|---|---|---|---|
| 1. Pioglitazone | PPAR γ (NR1C3) agonist | 2. Troglitazone | PPAR γ (NR1C3) agonist |
| 3. Capsaicin | PPAR γ (NR1C3) agonist | 4. Telmisartan | PPAR γ (NR1C3) agonist |
| 5. Gemfibrozil | PPAR α (NR1C1) agonist | 6. Fenofibrate | PPAR α (NR1C1) agonist |
| 7. Clofibrate | PPAR α (NR1C1) agonist | 8. Retinoic Acid | RXR/RAR agonist |
| 9. Bexarotene | RXR (NR1B family) agonist | 10. Bicalutamide | AR (NR3C4) antagonist |
| 11. Mifepristone | PR (NR3C3) agonist | 12. Dinoprostone | PR(NR3C3) agonist |
| 13. Megestrol Acetate | PR (NR3C3) agonist | 14. Letrozole | non-steroidal aromatase inhibitor |
| 15. Flufenamic acid | NSAID | 16. Tolfenamic acid | NSAID |
| 17. Mefenamic acid | NSAID | 18. Ketoprofen | NSAID |
| 19. Fenoprofen | NSAID | 20. Ibuprofen | NSAID |
| 21. Flurbiprofen | NSAID | 22. Nimesulide | NSAID |

TABLE 1-continued 42 hits were obtained screening the human PPARγ ligand trap fish line.

| # SM hit | Target/classification | # SM hit | Target/classification |
|---|---|---|---|
| 23. Indomethacin | NSAID | 24. Fentiazac | NSAID |
| 25. Rofecoxib | selective inhibitor of cyclo-oxygenase(COX) | 26. Bumetanide | Loop diuretic |
| 27. Ethacrynic Acid | Loop diuretic | 28. Cilnidipine | Calcium Channel Blocker |
| 29. Amlodipine | Calcium Channel Blocker | 30. Mycophenolate mofetil | Immunosuppressant |
| 31. Toltrazuril | Coccidiostat | 32. Diclazuril | Coccidiostat |
| 33. Selegiline | Monoamine oxidase inhibitors (MAOIs) inhibitor | 34. Vatalanib | small molecule protein kinase inhibitor |
| 35. 3-isobutyl-1-methylxanthine | phosphodiesterase inhibitor | 36. Anagrelide | phosphodiesterase inhibitor |
| 37. Succinylcholine | depolarizing muscle relaxant | 38. Pravastatin Lactone | Statins |
| 39. Idebenone | Anti-oxidant | 40. Taxol | mitotic inhibitor |
| 41. Terpenic lactones | Ginkgolide A | 42. Anethole-trithione | Anethole |

CoQ$_{10}$ and Other Benzoquinones Also Activate PPARγ

As suspected, treatment of the PPARγ LT line with water soluble CoQ$_{10}$ also resulted in similar spatial and quantitative levels of activation as observed with idebenone (FIG. 3). We also tested other ubiquinones: CoQ$_0$, CoQ$_1$, CoQ$_2$, mitoQ (10-[4,5-dimethoxy-2-methyl-3,6-dioxo-1,4-cyclo-heexadienl-yl]decyl triphenylphosphonium methanesulfonate) and the prototypical member of the class 1,4-benzoquinone. MitoQ, which is specifically targeted to mitochondria, failed to activate the PPARγ fish. CoQ$_0$, and CoQ$_1$ showed relatively weak activity, and CoQ$_2$ showed activity similar to idebenone and CoQ$_{10}$ (FIG. 3). 1,4-benzoquinone did not induce a detectable response, indicating that the 2,3-Dimethoxy-5-methyl-p additions are required for PPAR activation.

Idebenone and CoQ$_{10}$ Also Activate PPARα

Figure 5:
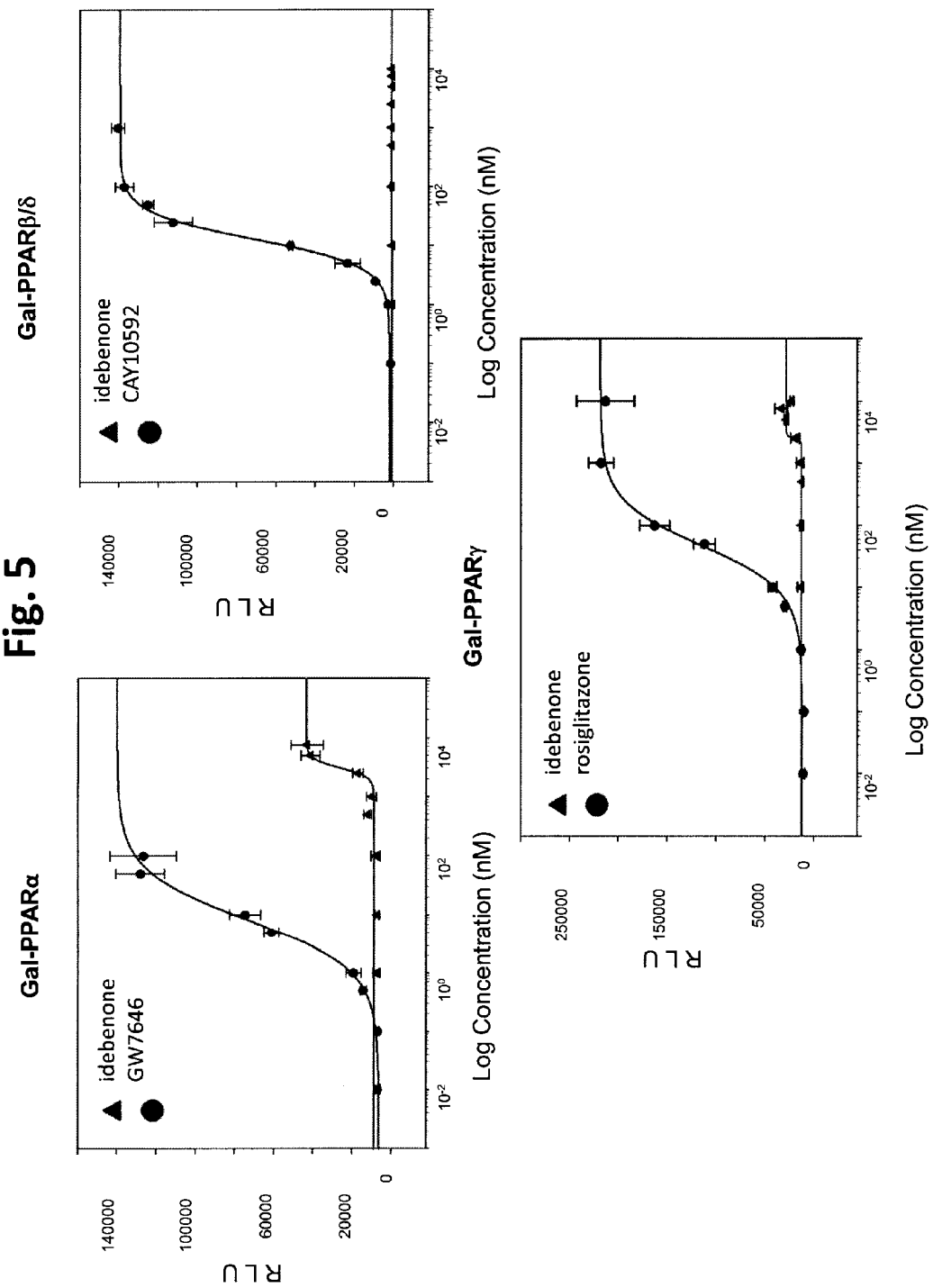
FIG. 5 shows that idebenone is a partial agonist of PPARα and PPARγ in human cells. Human HEK293 embryonic kidney cells were transfected with the ligand binding domains of hPPARα, hPPARδ/β and hPPARγ expression constructs and respective luciferase reporters. Treatment of the cells with the full agonists GW7647 (PPARα), CAY10592 (hPPARδ/β) or rosiglitazone (PPARγ) resulted in $EC_{50}$ concentrations of 8 nM, 12.8 nM and 48 nM respectively. Treatment with idebenone treatment resulted in an $EC_{50}$ of 3 μM for PPARα and 2.5 μM for PPARγ. Notably, however, maximum activation levels were far lower than elicited by the full agonists. Luciferase values were normalized for transfection efficiency using β-galactosidase and expressed as Relative Luciferase Units (RLU) from triplicate assays: Plasmids. pCMX, pcDNA3-GAL4-hPPARγ, pcDNA3-GAL4-hPPARα, UAS-luc, pGEM, pCMX-β-galactosidase.

To test for specificity, idebenone and CoQ$_{10}$ were also tested on PPARα, and PPARδ/β receptors in vivo and in vitro. While the PPARδ/β transgenic line showed no response to idebenone or CoQ$_{10}$, the PPARα line showed a robust response to both idebenone and CoQ$_{10}$ (FIG. 4). The same relative responses were obtained with HEK 293 cells grown in culture and transfected with PPAR expression vectors and luciferase reporters (FIG. 5). Notably, the idebenone responses were significantly lower than those obtained using the full agonists rosiglitazone and GW7647 (FIG. 5) consistent with the partial agonist activities observed in zebrafish. The EC$_{50}$'s obtained in fish and 293 cells for rosiglitazone are 13 nM and 47 nM and for idebenone 2 μM and 2.5 μM, respectively. As in zebrafish, PPARδ/β showed no response to idebenone when tested in cultured cells.

Idebenone and Ubiquinones Bind Directly to PPARα/γ

CoQ$_{10}$ is an oil-soluble, vitamin-like substance. The sizes, structures and properties of idebenone and CoQ$_{10}$ are comparable to those of other nuclear hormone receptor ligands, suggesting direct interactions within the ligand binding domain pockets of their NR targets. However, it is also possible that idebenone and ubiquinones bind elsewhere on the proteins, or act indirectly with no direct contact. To address this, we tested for direct binding via a number of assays.

Figure 6:
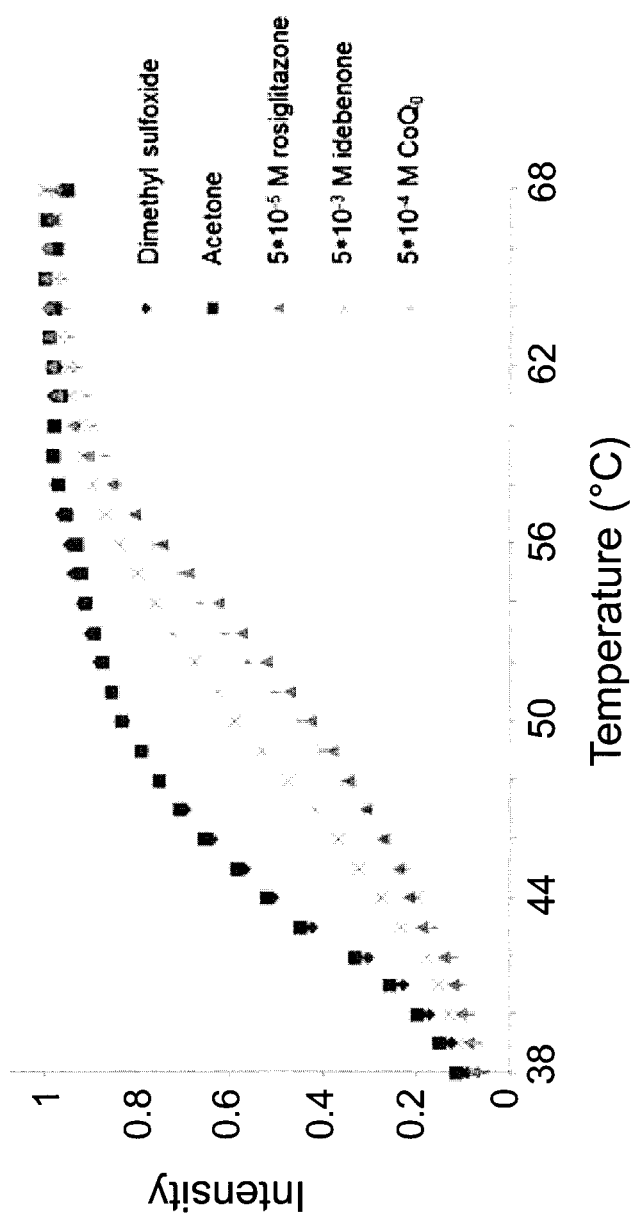
FIG. 6 illustrates thermostabilization of PPARγ by idebenone and $CoQ_0$. The PPARγ LBD (residues 206-477), expressed and purified from bacteria, was tested for thermostabilization by idebenone or $CoQ_0$ using the Stargazer thermostabilization assay. Specifically interacting molecules tend to increase thermal stability whereas non-specific interactions decrease thermal stability. Curves show the transition from native (transparent) to denatured (light scattering) conformations upon transition from 25° C. to 80° C. rosiglitazone (green), idebenone (purple) and $CoQ_0$ (blue) shifted the 50% native/denatured transition temperature by approximately 9.5, 5.5 and 8.5° C. respectively.

First, we used the in vitro Stargazer assay [34], which uses ligand-induced thermal stabilization to indicate the type of interaction (FIG. 6). A stabilizing shift in the thermal denaturation transition of 2° C. or more is typical for NR ligands [34]. Here, bacterially expressed and affinity purified PPARγ LBD showed strong thermal stabilization transitions of 9, 5.5 and 8.5° C. in the presence of rosiglitazone, idebenone and CoQ$_0$, respectively, whereas the vehicles, DMSO and acetone had no effect.

To see if idebenone can bind to directly to other PPAR LBDs, His-tagged PPARα, δ and γ LBDs were expressed in bacteria, Ni-NTA purified and incubated with 10 μM idebenone. After several washes in a 10 kDa cut off Amicon centrifuge filter (Millipore), lipids were extracted and analyzed by MS. These in vitro co-purifications confirmed strong binding of idebenone to the PPARα and PPARγ LBDs (FIG. 7A).

Next, we used the triple affinity-tagged Gal4/LBD fusion protein in our PPARγ LT fish line to see if idebenone could be co-purified from receptor bound in vivo. As controls, the multi-step affinity purifications were carried out using transgenic or wild-type fish treated with either rosiglitazone or idebenone. 1M salt was used in the lysate and during the affinity purifications to disrupt non-specific interactions. A two-step Flag/Strep purification from the PPARγ LT fish yielded >10$^5$ fold bait purification with a yield of 70%. The purified PPARγ or control purifications were then extracted with 2:1 chlorofonailmethanol, and the solvent phase analyzed by mass spectrometry. 1 gram of rosiglitazone treated PPARγ LT embryos was sufficient to produce a strong signal by MRM based mass spectrometry. Likewise, PPARγ LT fish treated with idebenone also yielded idebenone in the affinity purification eluate (FIG. 7B, C). Control purifications did not show significant binding of rosiglitazone or idebenone.

Idebenone does not Cause Lipid Deposition or Adipocyte Differentiation

Figure 8:
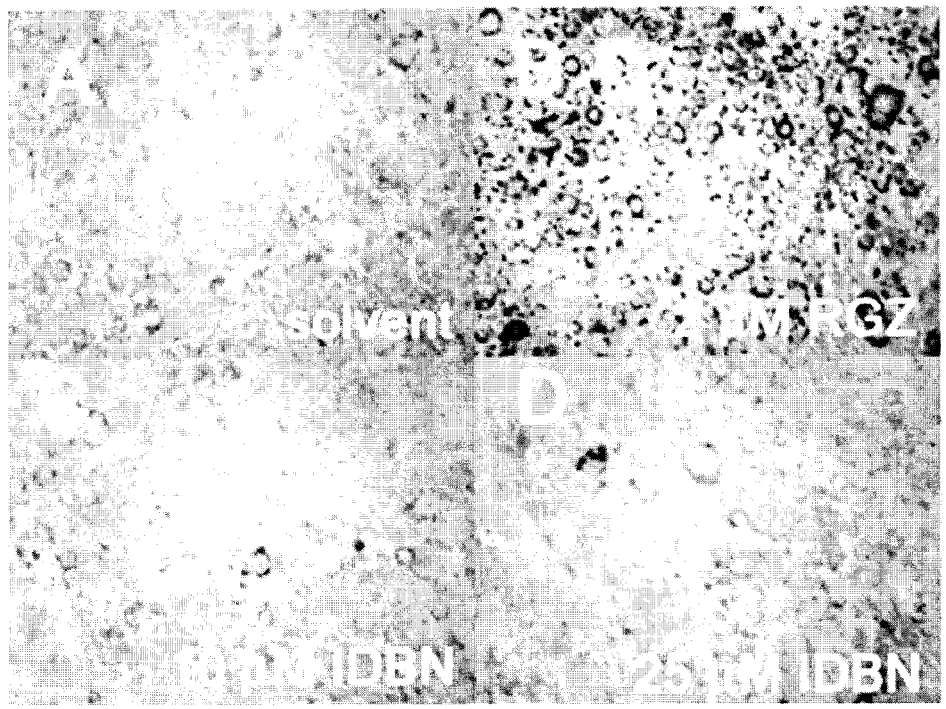
FIG. 8 demonstrates that idebenone does not induce lipid deposition or adipocyte differentiation. The treatment of murine pre-adipose 3T3-L1 with TZDs (e.g. rosiglitazone/panel B) in the presence of dexamethasone, isobutylmethylxanthine, and insulin results in the accumulation of intracellular lipids, induction of adipocyte specific genes and withdrawal from the cell cycle [42]. In contrast, cells treated with vehicle (DMSO; panel A) or idebenone (IDBN; panels C, D) showed no accumulation of lipid (Oil Red O staining).

One of the well-known detrimental side effects of TZDs is their induction of weight gain due to major increases in adipocyte numbers and lipid storage levels. Treating 3T3-L1 cells with rosiglitazone in culture has been used to model this effect. TZD treatment results in conversion of the cells to adipocytes with greatly increased lipid accumulation and storage (FIG. 8). As shown in FIG. 8c, d, this did not occur when treating cells with saturating levels of idebenone. Thus, as previously observed with other partial PPARγ partial agonists [23], idebenone does not stimulate adipocyte differentiation and activity.

Idebenone has Antidiabetic Properties in a Wild Type Mouse Model

We next investigated whether idebenone had antidiabetic properties in a diet induced obese C57BL/6J mouse model (FIG. 9). Mice started on high fat diet at the age of 6 weeks were treated by gavage at 16 weeks of age with vehicle, 30 mg/kilo (mpk) rosiglitzane or 50 mpk idebenone twice daily for 5 days. FIG. 9 shows that, like rosiglitazone, idebenone caused a trend towards lowered blood glucose levels (FIG. 9A), and a reduction in fasting insulin levels (FIG. 9B). Insulin resistance, as computed by HOMA-IR, also showed a clear improvement with idebenone (FIG. 9C).

Idebenone Improves Features of Non-alcoholic Fatty Liver Disease (NAFLD)

Non-alcoholic fatty liver disease (NAFLD) comprises a cluster of liver disorders of which the key feature is hepatic lipid accumulation (steatosis) in the absence of pathologies such as viral hepatitis or alcohol abuse. db/db mice fed on a 16% protein rodent diet (Harlan) supplemented with 10% sucrose reproduce many of the metabolic and histological disturbances seen in NAFDL patients. FIG. 10A shows a typical fatty liver isolated from a vehicle treated db/db mouse, with obvious enlargement and colour change. Addition of rosiglitazone to the food over a 3 week period caused a further 8.6% gain in liver weight (FIG. 10B). In contrast, treatment with idebenone reversed these histological NAFLD (FIG. 10A). In contrast, db/db mice treated with 900 or 1800 mpk idebenone for 3 weeks had 3% or 6.5% decrease in liver weight respectively in comparison to vehicle treated mice (FIG. 10B).

Figure 10:
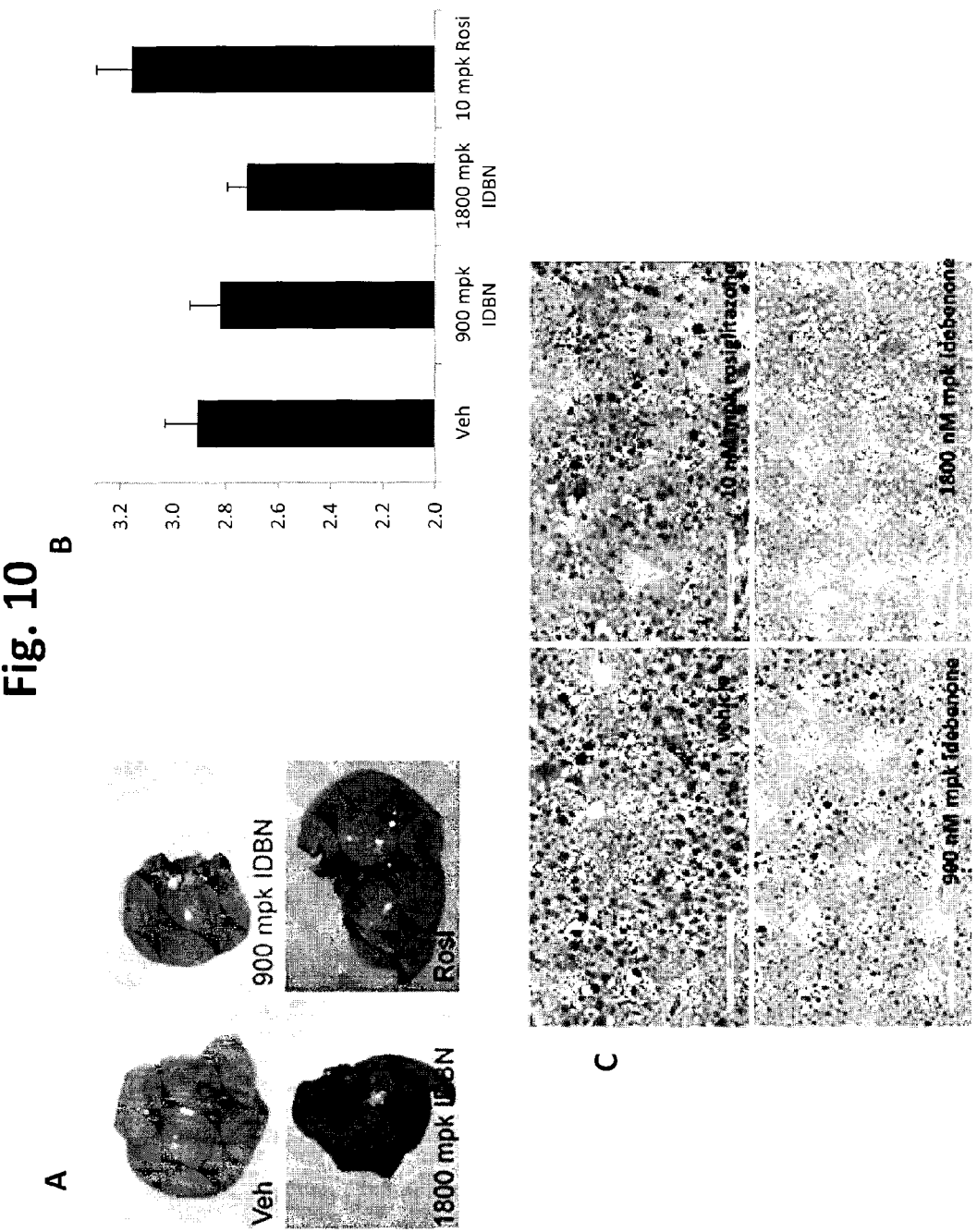
FIG. 10 demonstrates that idebenone improves features of Non-alcoholic fatty liver disease (NAFLD). Db/db mice were treated for 21 days with either vehicle, 10 mpk rosiglitazone, 900 mpk idebenone or 1800 mpk idebenone. A) Representative photomicrographs of livers of the 4 treatment groups are shown. B) Graph of liver weights of treatment groups. C) Representative photomicrographs depicting Oil Red O (ORO) staining of liver sections from vehicle, rosiglitazone or idebenone treated db/db mice. Lipid content was significantly higher in vehicle- and rosiglitazone-treated db/db mice. Three weeks after treatment with idebenone there was a significant dose dependent decrease in fat compared to vehicle and rosiglitazone treated db/db mice. D) Relative levels of reactive oxygen species were detected using thiobarbituric acid-reactive substances (TBARS), as described in the material and methods. E) Relative mRNA expression levels of the PPAR target genes ADFP and PLIN4 as determined by QPCR.
Figure 10:
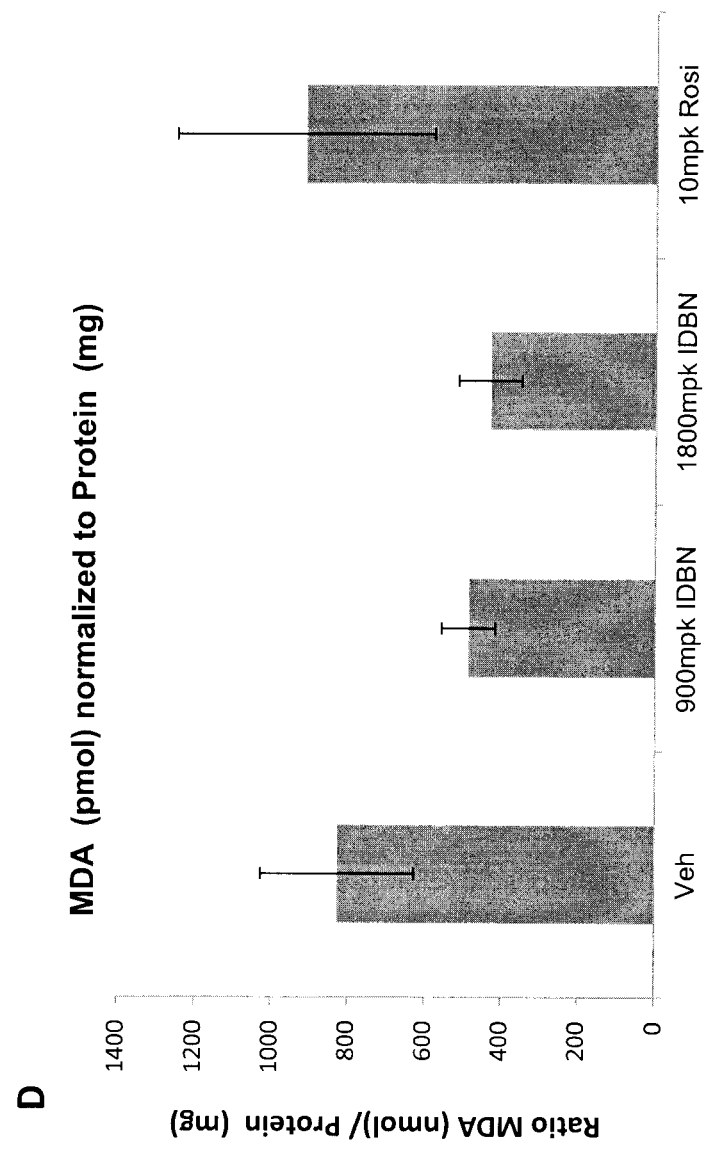
Figure 10:
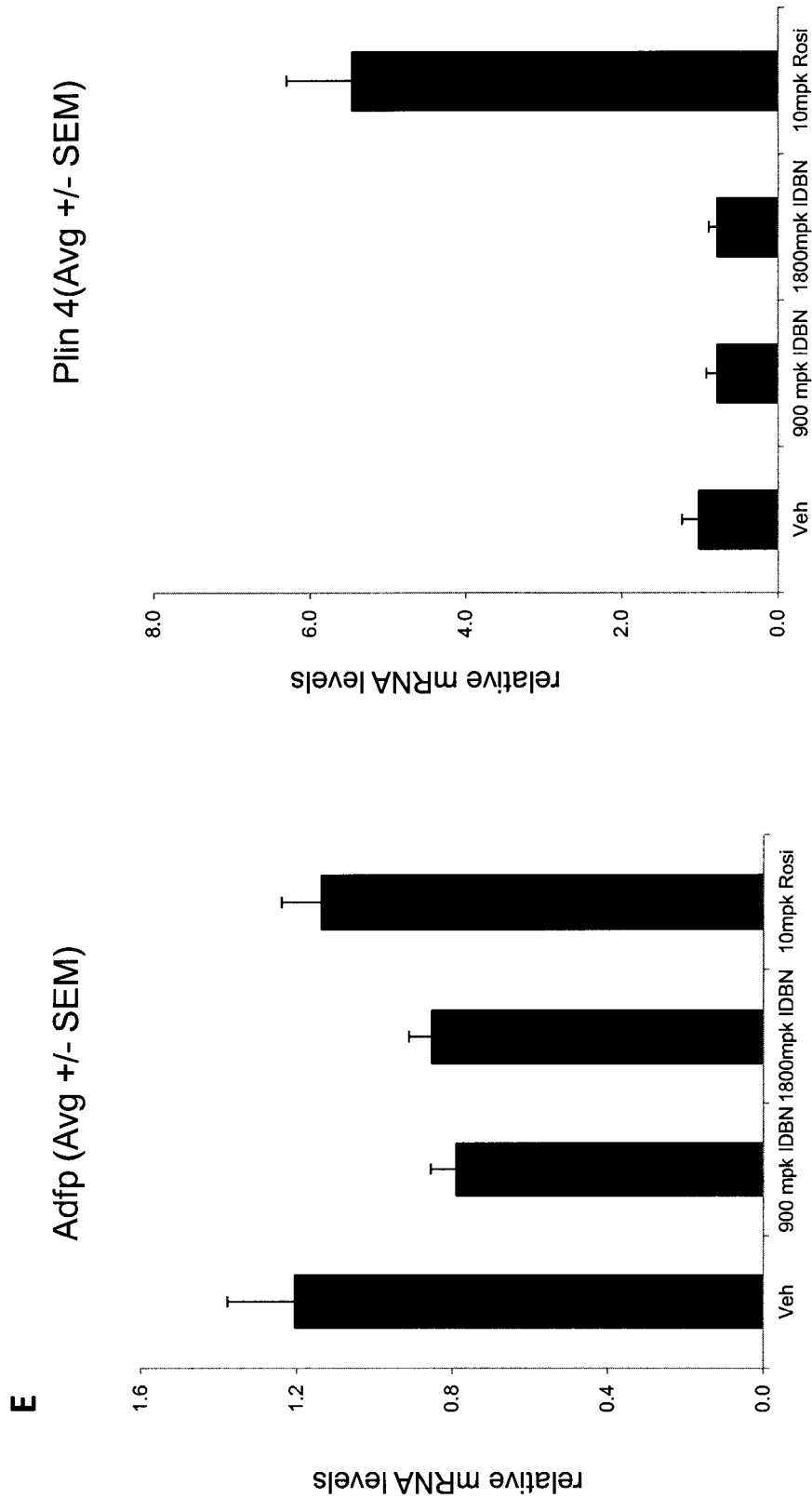

Similarly, oil-red-O (ORO) staining of liver sections showed that lipid content was significantly higher in vehicle and rosiglitazone db/db mice. After 21 days of idebenone administration, however, there was a significant dose-dependent decrease in fat compared to vehicle- and rosiglitazone-treated db/db mice (FIG. 10 C).

Oxidative stress plays an important role in the pathogenesis of NASH. Therefore we measured TBARS in liver homogenates. As indicated by the accumulation of TBARS (MBA), lipid peroxides were only reduced in the livers of idebenone treated db/db mice (FIG. 10 D).

The expression of genes encoding perilipin proteins, such as ADFP and PLIN4, both implicated in lipid droplet formation, are markers of steatosis. These genes were down regulated in livers of idebenone treated animals, whereas rosiglitazone upregulated PLIN4 strongly. A decreased expression of ADFP and PLIN4 in livers of idebenone treated mice indicates a reversal of steatosis and diminution of triglyceride content (FIG. 10 E).

Idebenone has Anti-inflammatory Properties Through PPARα and/or PPARγ Activation Previous studies have shown that PPAR agonists have anti-inflammatory properties, and can be used to treat a variety of inflammatory responses. To test if this is also true for idebenone, we used a zebrafish model of inflammation [47]. Exposure of fish larvae to copper sulfate causes non-invasive damage to neuromast cells, which form external clusters along the lateral midline. This inflammation can be visualized via the recruitment of GFP-expressing leukocytes [47]. As expected, this recruitment of GFP positive cells could be alleviated by addition of the known anti-inflammatory agent ibuprofen (FIG. 11). Similarly, idebenone also acted as a robust anti-inflammatory agent, with activity detectable at sub micromolar concentrations (FIGS. 11 A and B).

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

REFERENCES

1. Pardee, K., A. S. Necakov, and H. Krause, *Nuclear Receptors: Small Molecule Sensors that Coordinate Growth, Metabolism and Reproduction.* Subcell Biochem, 2011. 52: p. 123-53.
2. Giguere, V., *Orphan nuclear receptors: from gene to function.* Endocr Rev, 1999. 20(5): p. 689-725.
3. Kersten, S., B. Desvergne, and W. Wahli, *Roles of PPARs in health and disease.* Nature, 2000. 405(6785): p. 421-4.
4. Mangelsdorf, D. J., et al., *The nuclear receptor superfamily: the second decade.* Cell, 1995. 83(6): p. 835-9.
5. Meyer, C. A., Q. Tang, and X. S. Liu, *Minireview: applications of next-generation sequencing on studies of nuclear receptor regulation and function.* Mol Endocrinol, 2012. 26(10): p. 1651-9.
6. Chawla, A., et al., *Nuclear receptors and lipid physiology: opening the X-files.* Science, 2001. 294(5548): p. 1866-70.
7. Chen, T., *Nuclear receptor drug discovery.* Curr Opin Chem Biol, 2008. 12(4): p. 418-26.
8. Barish, G. D., V. A. Narkar, and R. M. Evans, *PPAR delta: a dagger in the heart of the metabolic syndrome.* J Clin Invest, 2006. 116(3): p. 590-7.
9. Girnun, G. D., et al., *APC-dependent suppression of colon carcinogenesis by PPARgamma.* Proc Natl Acad Sci USA, 2002. 99(21): p. 13771-6.
10. Mueller, E., et al., *Effects of ligand activation of peroxisome proliferator-activated receptor gamma in human prostate cancer.* Proc Natl Acad Sci USA, 2000. 97(20): p. 10990-5.
11. Nicol, C. J., et al., *PPARgamma influences susceptibility to DMBA-induced mammary, ovarian and skin carcinogenesis.* Carcinogenesis, 2004. 25(9): p. 1747-55.
12. Sabatino, L., et al., *A novel peroxisome proliferator-activated receptor gamma isoform with dominant negative activity generated by alternative splicing.* J Biol Chem, 2005. 280(28): p. 26517-25.
13. Sarraf, P., et al., *Loss-of-function mutations in PPAR gamma associated with human colon cancer.* Mol Cell, 1999. 3(6): p. 799-804.
14. Tontonoz, P. and B. M. Spiegelman, *Fat and beyond: the diverse biology of PPARgamma.* Annu Rev Biochem, 2008. 77: p. 289-312.
15. Altmann, R., et al., *13-Oxo-ODE is an endogenous ligand for PPARgamma in human colonic epithelial cells.* Biochem Pharmacol, 2007. 74(4): p. 612-22.
16. Keelan, J., et al., *15-deoxy-delta12,14-prostaglandin J2-induced apoptosis in amnion-like WISH cells.* Prostaglandins Other Lipid Mediat, 2001. 66(4): p. 265-82.
17. McIntyre, T. M., et al., *Identification of an intracellular receptor for lysophosphatidic acid (LPA): LPA is a transcellular PPARgamma agonist.* Proc Natl Acad Sci USA, 2003. 100(1): p. 131-6.
18. Forman, B. M., et al., *15-Deoxy-delta 12, 14-prostaglandin J2 is a ligand for the adipocyte determination factor PPAR gamma.* Cell, 1995. 83(5): p. 803-12.
19. Kliewer, S. A., et al., *A prostaglandin J2 metabolite binds peroxisome proliferator-activated receptor gamma and promotes adipocyte differentiation. Cell,* 1995. 83(5): p. 813-9.

20. Chakravarthy, M. V., et al., *Identification of a physiologically relevant endogenous ligand for PPARalpha in liver.* Cell, 2009. 138(3): p. 476-88.
21. Devchand, P. R., et al., *The PPARalpha-leukotriene B4 pathway to inflammation control.* Nature, 1996. 384 (6604): p. 39-43.
22. McCarthy, F. P., et al., *PPAR-gamma—a possible drug target for complicated pregnancies.* Br J Pharmacol, 2013. 168(5): p. 1074-85.
23. Rodriguez-Rivera, J., L. Denner, and K. T. Dineley, *Rosiglitazone reversal of Tg2576 cognitive deficits is independent of peripheral gluco-regulatory status.* Behav Brain Res, 2011. 216(1): p. 255-61.
24. Velez, L. M., G. A. Abruzzese, and A. B. Motta, *The biology of the peroxisome proliferator-activated receptor system in the female reproductive tract.* Curr Pharm Des, 2013. 19(25): p. 4641-6.
25. Belfort, R., et al., *A placebo-controlled trial of pioglitazone in subjects with nonalcoholic steatohepatitis.* N Engl J Med, 2006. 355(22): p. 2297-307.
26. Rogue, A., et al., *PPAR agonists reduce steatosis in oleic acid-overloaded HepaRG cells.* Toxicol Appl Pharmacol, 2014.
27. Krentz, A. J. and P. S. Friedmann, *Type 2 diabetes, psoriasis and thiazolidinediones.* Int J Clin Pract, 2006. 60(3): p. 362-3.
28. Boris, M., et al., *Effect of pioglitazone treatment on behavioral symptoms in autistic children.* J Neuroinflammation, 2007. 4: p. 3.
29. Abbas, A., et al., *PPAR-gamma agonist in treatment of diabetes: cardiovascular safety considerations.* Cardiovasc Hematol Agents Med Chem, 2012. 10(2): p. 124-34.
30. Liu, L., et al., *Rosiglitazone inhibits bone regeneration and causes significant accumulation of fat at sites of new bone formation.* Calcif Tissue Int, 2012. 91(2): p. 139-48.
31. Shah, P. and S. Mudaliar, *Pioglitazone: side effect and safety profile.* Expert Opin Drug Saf, 2010. 9(2): p. 347-54.
32. Choi, J. H., et al., *Antidiabetic actions of a non-agonist PPARgamma ligand blocking Cdk5-mediated phosphorylation.* Nature, 2011. 477(7365): p. 477-81.
33. Monks, T. J., et al., *Quinone chemistry and toxicity.* Toxicol Appl Pharmacol, 1992. 112(1): p. 2-16.
34. Okamoto, K., et al., *Synthesis, metabolism, and in vitro biological activities of 6-(10-hydroxydecyl)-2,3-dimethoxy-5-methyl-1,4-benzoquinone (CV-2619)-related compounds.* Chem Pharm Bull (Tokyo), 1988. 36(1): p. 178-89.
35. Chang, Y., Y. W. Lin, and S. J. Wang, *Idebenone inhibition of glutamate release from rat cerebral cortex nerve endings by suppression of voltage-dependent calcium influx and protein kinase A.* Naunyn Schmiedebergs Arch Pharmacol, 2011. 384(1): p. 59-70.
36. Suno, M. and A. Nagaoka, *Inhibition of lipid peroxidation by a novel compound, idebenone (CV-2619).* Jpn J Pharmacol, 1984. 35(2): p. 196-8.
37. Gutzmann, H. and D. Hadler, *Sustained efficacy and safety of idebenone in the treatment of Alzheimer's disease: update on a 2-year double-blind multicentre study.* J Neural Transm Suppl, 1998. 54: p. 301-10.
38. Rudolph, G., et al., *Effects of idebenone on color vision in patients with leber hereditary optic neuropathy.* J Neuroophthalmol, 2013. 33(1): p. 30-6.
39. Becker, C., K. Bray-French, and J. Drewe, *Pharmacokinetic evaluation of idebenone.* Expert Opin Drug Metab Toxicol, 2010. 6(11): p. 1437-44.
40. Buyse, G. M., et al., *Idebenone as a novel, therapeutic approach for Duchenne muscular dystrophy: results from a 12 month, double-blind, randomized placebo-controlled trial.* Neuromuscul Disord, 2011. 21(6): p. 396-405.
41. Napolitano, A., et al., *Long-term treatment with idebenone and riboflavin in a patient with MELAS.* Neurol Sci, 2000. 21(5 Suppl): p. S981-2.
42. Tontonoz, P., et al., *Terminal differentiation of human liposarcoma cells induced by ligands for peroxisome proliferator-activated receptor gamma and the retinoid X receptor.* Proc Natl Acad Sci USA, 1997. 94(1): p. 237-41.
43. Westerfield, M., *The zebrafish book a guide for the laboratory use of zebrafish (Danio rerio).* 3rd ed. 1993, Eugene, Oreg.: Univ. of Oregon.
44. Tiefenbach, J., et al., *A live zebrafish-based screening system for human nuclear receptor ligand and cofactor discovery.* PLoS One, 2010. 5(3): p. e9797.
45. Reinking, J., et al., *The Drosophila nuclear receptor e75 contains heme and is gas responsive.* Cell, 2005. 122(2): p. 195-207.
46. Carleton, H. M., *Carleton's histological technique.* 5. ed. 1980.
47. d'Alencon, C. A., et al., *A high-throughput chemically induced inflammation assay in zebrafish.* BMC Biol, 2010. 8: p. 151.

The invention claimed is:

1. A method of treating non-alcoholic fatty liver disease comprising: identifying a mammal having non-alcoholic fatty liver disease; and administering a therapeutically effective amount of idebenone to the mammal.

2. The method of claim 1, wherein the mammal has steatohepatitis.

3. The method of claim 1, wherein the idebenone is orally administered to the mammal.

4. The method of claim 1, wherein the idebenone is administered as a composition consisting of idebenone and a pharmaceutically acceptable carrier.

5. A method of treating a mammal having non-alcoholic fatty liver disease, comprising administering a therapeutically effective amount of idebenone to the mammal.

* * * * *